United States Patent
Saigal et al.

(10) Patent No.: US 7,196,216 B2
(45) Date of Patent: Mar. 27, 2007

(54) PROCESS FOR PREPARATION OF GABAPENTIN

(75) Inventors: Jagdish Chand Saigal, Maharashtra (IN); Rajender Pershad Gupta, Maharashtra (IN); Rajesh Vinodrai Naik, Maharashtra (IN); Araddy Rajshekhar, Karnataka (IN); Rajesh Dilip Joshi, Maharashtra (IN)

(73) Assignee: Nicholas Piramal India Limited, Maharashtra ( * ) Notice: Subject to any disclaimer, the term of this patent is extended or adjusted under 35 U.S.C. 154(b) by 105 days.

(21) Appl. No.: 10/497,899

(22) PCT Filed: Nov. 18, 2002

(86) PCT No.: PCT/IN02/00221

§ 371 (c)(1),
(2), (4) Date: Jun. 3, 2004

(87) PCT Pub. No.: WO2004/046084

PCT Pub. Date: Jun. 3, 2004

(65) Prior Publication Data

US 2005/0119503 A1    Jun. 2, 2005

(51) Int. Cl.
*C07C 61/08* (2006.01)
(52) U.S. Cl. ..................................... 562/507
(58) Field of Classification Search ............. 562/507, 562/509, 553, 554
See application file for complete search history.

(56) References Cited

U.S. PATENT DOCUMENTS 4,024,175 A    5/1977    Satzinger et al.
4,894,476 A    1/1990    Butler et al.
5,068,413 A    11/1991   Steiner et al.
5,095,148 A    3/1992    Mettler et al.
5,132,451 A    7/1992    Jennings et al.
6,255,526 B1 *  7/2001   Pesachovich et al. ....... 562/507
6,576,790 B1 *  6/2003   Tenconi et al. ............. 562/507

FOREIGN PATENT DOCUMENTS

| EP | 0 340 677 A2 | 11/1989 |
| WO | WO 98/28255 | 7/1998 |
| WO | WO 02/44123 A1 | 6/2000 |
| WO | WO 00/58268 | 10/2000 |

OTHER PUBLICATIONS

Kirk-Othmer Encyclopedia of Chemical Technology © 1993 by John Wiley & Sons, Inc. All Online Posting Date: Aug. 17, 2001.*

* cited by examiner

*Primary Examiner*—Thurman K. Page
*Assistant Examiner*—Karl J. Puttlitz
(74) *Attorney, Agent, or Firm*—Timothy J. Martin; Michael R. Henson; John W. Carpenter

(57) ABSTRACT

A process for producing gabapentin, (1-(aminomethyl)-1-cyclohexaneacetic acid) from gabapentin hydrochloride salt. In the disclosed process, the gabapentin hydrochloride is converted to gabapentin using an inorganic base, such as barium hydroxide. Gabapentin hydrochloride is converted to gabapentin sulfate which in turn is converted to free base using barium hydroxide. The process is directed to improvement in the manufacture of gabapentin which would be industrially feasible and effective. Gabapentin obtained following the process of the invention is suitable as a drug especially in the treatment of cerebral diseases such as epilepsy.

29 Claims, No Drawings

PROCESS FOR PREPARATION OF GABAPENTIN

This application is a 371 of PCT/IN02/00221, filed on Nov. 11, 2002.

FIELD OF THE INVENTION

The present invention relates to a process for producing Gabapentin, 1-(aminomethyl)-1-cyclohexaneacetic acid from Gabapentin hydrochloride salt. The process is directed to improvement in the manufacture of Gabapentin which would be industrially feasible and facilitate simple and cost-effective manufacture of Gabapentin. Gabapentin obtained following the process of the invention is suitable as a drug especially in the treatment of cerebral diseases such as epilepsy.

BACKGROUND OF THE INVENTION

Gabapentin, 1-(aminomethyl)-1-cyclohexaneacetic acid is known to have the chemical structure as hereunder:

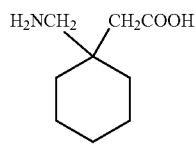

Fig. 1

Gabapentin is used in the treatment of cerebral diseases such as epilepsy. There are various methods presently known for preparing Gabapentin from a variety of starting materials. U.S. Pat. No. 4,024,175 describes at least three methods of preparing Gabapentin from cyclohexyl-1,1-diacetic acid. Each of these methods results in the formation of Gabapentin hydrochloride salt, which may be converted to 1-(aminomethyl)-1-cyclohexaneacetic acid by treatment with a basic ion exchanger and then crystallized from a solvent such as ethanol/ether.

U.S. Pat. No. 4,894,476 specifically discloses an improved method for converting the hydrochloride salt into the free amino acid. This involves pouring a deionized water solution of the salt over an ion exchange column, eluting with deionized water, producing a slurry from the elute, adding an alcohol to the slurry, centrifuging and drying the slurry to obtain the free amino acid.

Alternative methods for preparing Gabapentin have been described that do not proceed via the hydrochloride or any other mineral acid salt. Such methods include those described in U.S. Pat. Nos. 5,132,451, 5,095,148, 5,068,413. Each of these methods involve a cyanic intermediate which is hydrogenated under severe conditions to produce the free amino acid.

These methods are industrially impractical. Those methods comprising ion exchange columns require the use of large amounts of ion exchanger for lengthy periods of time to lower the level of chloride ions to the desired level. The alternative methods involve further more demanding steps.

WO 98/28255 describes the preparation of Gabapentin from Gabapentin hydrochloride through optional pre-treatment to remove inorganic salts and then by treating suitable organic amines like triethylamine, tributylamine, tripropylamine, trihexylamine, diethylamine, ethanolamine and benzylamine. Preferably the amine is tributylamine.

OBJECTS OF THE INVENTION

It is thus the basic object of the present invention to provide a process of producing Gabapentin which would be simple and avoid the aforediscussed problems of the known art.

Another object of the present invention is directed to a process for the manufacture of Gabapentin from Gabapentin hydrochloride salt which would avoid severe conditions and/or complexities and can be readily adopted for industrial application.

Yet further object of the present invention is directed to provide a method of manufacture of Gabapentin which would have good yield and not involve lengthy extended process steps.

Yet another object of the present invention is to provide a method of manufacture of Gabapentin which would be cost-effective and can be carried out involving simple and readily available ingredients starting material.

SUMMARY OF THE INVENTION

Thus according to the present invention there is provided a process of producing Gabapentin comprising:
  i) providing an aqueous alkaline solution of Gabapentin Hydrochloride salt and reacting with Sulfuric acid followed by neutralizing with inorganic base;
  ii) filtration of inorganic salts and distillation to obtain a resultant solid;
  iii) dissolving the said resultant solid of (ii) above in an protic solvent, filtering to remove further inorganic salts followed by distillation of the resulting solvent to obtained a residue;
  iv) adding another solvent to said residue and isolating Gabapentin therefrom by filtration.

In the above process the inorganic bases can be selected from metal hydroxide or carbonate of IIa of periodic table preferably barium hydroxide.

The alkali used in the process can be selected from such as Sodium hydroxide, Potassium hydroxide, Calcium hydroxide and alkali metal hydroxides, carbonates.

The first solvents employed can be selected from Methanol, Acetonitrile, Isopropyl alcohol, acetone.

The 'second' solvent can be selected from Isopropanol, acetone, Methanol, Acetonitrile, Dimethylformamide, Ethyl Acetate, Diisopropylether, Methylene chloride.

The above process of the present invention provide an improved, industrially feasible method for preparing Gabapentin from Gabapentin hydrochloride. The process avoids the disadvantages associated with prior art methods and selectively employs the inorganic bases to convert Gabapentin hydrochloride to Gabapentin. Gabapentin hydrochloride used in the process can be prepared by the method known in prior art such as U.S. Pat. No. 4,152,326 (1979).

DETAILED DESCRIPTION OF THE INVENTION

In accordance with a preferred aspect the process of the invention comprises:
  (1) mixing aqueous solution of the Gabapentin hydrochloride with alkali;
  (2) filtration to separate solid and heating with dil. Sulfuric acid followed by pH adjustment to neutral with inorganic bases at 30–80° C.
  (3) filtration of inorganic salts in particular sulfate and concentration of filtrate under vacuum.

(4) redissolving the resultant solid in protic solvent (first solvent).
(5) filtration of traces of inorganic salt in particular sulfate salts if any.
(6) concentration of protic solvent to dryness.
(7) addition of second solvent and isolation of Gabapentin by filtration.

Thus the initial critical stages of the process of the present invention comprises of mixing of an aqueous solution of Gabapentin hydrochloride with alkali metal hydroxide or carbonate solutions. Filtration of separated solids and reacting with dil. Sulfuric acid and then adjusting pH to neutral with inorganic base.

The subsequent critical steps of the process is the removal of water by distillation from the filtrate after filtration of corresponding sulfate salt. The water may be distilled off at atmospheric pressure or under vacuum. The next step involves the addition of protic solvent (first solvent) to dissolve Gabapentin and filtration of traces of, if any, corresponding sulfate salt. In the next step the solvent from the filtrate is removed and addition of 'second' solvent and filtration of Gabapentin. The solvent may be distilled at atmospheric pressure or under vacuum.

Preferably, the Gabapentin hydrochloride salt is used as a solution in water in concentration ranging from 10 to 40%, more preferably 33%.

The inorganic bases are preferably used as solid and/or as aqueous solution of concentration 5 to 15% more preferably 10%.

The temperature of neutralization is selected from RT 30° C. to 80° C. preferably 40° C. the final pH of the neutralization is about 5 to 8 preferably 7.

The process of the invention, its objects and advantages are explained hereunder in greater detail by way of the non-limiting exemplary illustrations of the process as discussed hereunder:

EXAMPLE 1

Gabapentin hydrochloride (10 g.) was dissolved in water 30 ml. and heated to 40–60° C. To this solution was added Sodium hydroxide to pH 9.0 to 14.0 and the reaction mixture heated at 40–60° C. for 3 to 6 hrs. The reaction mass is cooled to 5–10° C. and maintained at this temperature for 6 hrs. The separated solid is filtered and added to dil. Sulfuric acid 30 ml. (5 ml. Sulfuric acid diluted to 30 ml. with water).

The reaction mixture heated under reflux for 12 hrs. and then cooled to 30° C. The pH of the solution was adjusted to 7.0 to 7.5 with barium hydroxide suspension in water. The separated barium sulfate is filtered off and wash with water 10 ml. The filtrate is concentrated to dryness under vacuum. Methanol (120 ml.) added to the residue and then clear solution is filtered through Celite. Methanol is recovered under vacuum at below 50° C. The product remained was treated with Iso-propanol (50 ml.), stirred of 30 min. at RT and filtered off. The product obtained is dried till content weight of 6.7 g.

EXAMPLES 2–9

The method of Example 1 was followed using different solvents shown in Table 1 alongwith percentage yield (w/w)

TABLE 1

| Example No. | First Solvent | Second Solvent | Yield (w/w) % |
| --- | --- | --- | --- |
| 2 | Methanol | Methanol | 55 |
| 3 | Methanol | IPA | 67 |
| 4 | Methanol | Acetone | 65 |
| 5 | Methanol | Acetonitrile | 52 |
| 6 | Acetonitrile | Methanol | 53 |
| 7 | Acetonitrile | IPA | 64 |
| 8 | Acetonitrile | Acetone | 65 |
| 9 | Acetonitrile | Acetonitrile | 51 |

Importantly, the various options of the first and second solvents tried as above in accordance with the process of the invention have demonstrated good yield by way of a simple and cost effective process. The above exemplary illustrations also demonstrate the simplicity on the process and the possible avoiding of complexity involved in manufacture of Gabapentin from Gabapentin hydrochloride salt. The process is industrially viable and should serve in wide-scale manufacture of Gabapentin especially for its drug/medicinal applications/end uses.

The invention claimed is:
1. A process of producing gabapentin comprising:
   i) providing an aqueous alkaline solution of gabapentin hydrochloride salt, forming a solid therefrom and reacting said solid with sulfuric acid to form a salt followed by neutralizing with inorganic bases;
   ii) filtration of inorganic salts and distillation to obtain a resultant solid;
   iii) dissolving the said resultant solid of (ii) above in an protic solvent, filtering to removing traces of inorganic salts followed by distillation of the resulting solvent to obtained a residue;
   iv) adding another solvent to said residue and isolating gabapentin therefrom by filtration.
2. A process as claimed in claim 1 wherein:
   (1) step (i) is accomplished by mixing an aqueous solution of the gabapentin hydrochloride with an alkali followed by filtration to separate solids therefrom and thereafter mixing said solids with dilute sulfuric acid and heating, and the step of neutralizing with inorganic bases is accomplished by pH adjustment to neutral with inorganic bases at 30–80° C.,
   (2) the step of filtration of inorganic salts and distillation is accomplished by filtration of inorganic salts, including sulfates, and concentration of filtrate under vacuum to obtain a resultant solid,
   (3) redissolving the resultant solid in protic solvent,
   (4) filtration of traces of inorganic salt in particular sulfate salt if any,
   (5) concentration of protic solvent to dryness, and
   (6) addition of second solvent and isolation of gabapentin by filtration.
3. A process as claimed in claim 2 wherein the alkali used to form the aqueous alkaline solution is selected from a group consisting of sodium hydroxide, potassium hydroxide, calcium hydroxide, other alkali metal hydroxides, and carbonates.
4. A process as claimed in claim 2 wherein the inorganic bases are selected from metal hydroxides and carbonates of group IIa of the Periodic Table.
5. A process as claimed in claim 2 wherein the temperature of neutralization is maintained between about 30° C. to 80° C.

6. A process as claimed in claim 5 wherein the temperature of neutralization is maintained at 40° C.

7. A process as claimed in claim 1 wherein the inorganic bases are selected from metal hydroxides and carbonates of group IIa of the Periodic Table.

8. A process as claimed in claim 1 wherein the gabapentin salts are used as a solution in water in concentration ranging from 10% to 40%.

9. A process as claimed in claim 8 wherein the concentration of the aqueous solution is about 33%.

10. A process as claimed in claim 1 wherein the inorganic base is barium hydroxide.

11. A process as claimed in claim 1 wherein the inorganic bases are used as solids and/or as aqueous solutions of concentrations in a range of about 5% to 15%.

12. A process as claimed in claim 11 wherein the inorganic bases are used as solids and/or as aqueous solutions of concentration of about 10%.

13. A process as claimed in claim 1 wherein the temperature of neutralization is maintained between about 30° C. to 80° C.

14. A process as claimed claim 1 wherein the final pH of the neutralization is about 5 to 8.

15. A process as claimed in claim 14 wherein the final pH of the neutralization is about 7.

16. A process as claimed in claim 1 wherein the protic solvent is selected from a group consisting of methanol, acetonitrile, isopropyl alcohol, and acetone.

17. A process as claimed in claim 16 wherein the protic solvent is methanol.

18. A process as claimed in claim 1, wherein the said another solvent is selected from a group consisting of isopropanol, acetone, methanol, acetonitrile, dimethylformamide, ethyl acetate, diisopropylether, and methylene chloride.

19. The process as claimed in claim 18, wherein the said another solvent is isopropanol.

20. A process of producing gabapentin comprising:
(A) providing an aqueous alkaline solution of gabapentin hydrochloride salt and thereafter obtaining solids therefrom;
(B) mixing the solids with sulfuric acid and adding an inorganic base thereto to obtain a first intermediate solution;
(C) filtering inorganic salts from the first intermediate solution to form a first filtrate;
(D) concentrating the first filtrate to obtain a first residue;
(E) dissolving said first residue in a protic solvent to form a second intermediate solution;
(F) filtering the second intermediate solution to remove traces of inorganic salts to obtain a second filtrate;
(G) concentrating said second filtrate to obtain a second residue; and
(H) placing said second residue in a selected solvent and recovering gabapentin therefrom.

21. A process as claimed in claim 20 wherein:
(1) the step of providing an aqueous alkaline solution of gabapentin hydrochloride salt and thereafter obtaining solids therefrom is accomplished by mixing an aqueous solution of gabapentin hydrochloride with an alkali followed by filtration to separate solids therefrom;
(2) the step of mixing the solids with sulfuric acid is accomplished by mixing the solids with dilute sulfuric acid and heating;
(3) the step of adding an inorganic base is accomplished to achieve pH adjustment to about neutral at a temperature of about 30–80° C.; and
(4) the step of concentrating said second filtrate is accomplished by distillation to dryness.

22. A process as claimed in claim 20 wherein said alkali is selected from a group consisting of sodium hydroxide, potassium hydroxide, calcium hydroxide, other alkali metal hydroxides, and carbonates.

23. A process as claimed in claim 20 wherein the inorganic bases are selected from metal hydroxides and carbonates of group IIa of the Periodic Table.

24. A process as claimed in claim 20 wherein the gabapentin salts are used as a solution in water in a concentration ranging from about 10 to 40%.

25. A process as claimed in claim 20 wherein the inorganic base is barium hydroxide.

26. A process as claimed in claim 20 wherein the first intermediate solution is achieved and maintained at a temperature between about 30° C. to 80° C.

27. A process as claimed claim 20 wherein the final pH of the first intermediate solution following addition of the inorganic base is about 5 to 8.

28. A process as claimed in claim 20 wherein the protic solvent is selected from a group consisting of methanol, acetonitrile, isopropyl alcohol, and acetone.

29. A process as claimed in claim 20 wherein the second solvent is selected from a group consisting of isopropanol, acetone, methanol, acetonitrile, dimethylformamide, ethyl acetate, diisopropylether, and methylene chloride.

* * * * *